(12) United States Patent
Moctezuma de La Barrera (10) Patent No.: US 8,007,448 B2
(45) Date of Patent: Aug. 30, 2011

(54) SYSTEM AND METHOD FOR PERFORMING ARTHROPLASTY OF A JOINT AND TRACKING A PLUMB LINE PLANE

(75) Inventor: Jose Luis Moctezuma de La Barrera, Freiburg (DE)

(73) Assignee: Stryker Leibinger GmbH & Co. KG., Freiburg (DE)

(*) Notice: Subject to any disclaimer, the term of this patent is extended or adjusted under 35 U.S.C. 154(b) by 1563 days.

(21) Appl. No.: 10/961,455

(22) Filed: Oct. 8, 2004

(65) Prior Publication Data
US 2006/0095047 A1    May 4, 2006

(51) Int. Cl.
*A61B 5/103* (2006.01)
(52) U.S. Cl. ............ 600/587; 600/426; 606/102
(58) Field of Classification Search ............ 606/102; 623/23.4; 600/424–428, 587
See application file for complete search history.

(56) References Cited

U.S. PATENT DOCUMENTS

| | | | |
|---|---|---|---|
| 4,323,459 A | 4/1982 | Quinlan | 210/700 |
| 4,396,945 A | 8/1983 | DiMatteo et al. | 358/107 |
| 4,722,056 A | 1/1988 | Roberts et al. | 364/413 |
| 4,869,247 A | 9/1989 | Howard, III et al. | 128/303.1 |
| 4,923,459 A | 5/1990 | Nambu | 606/130 |
| 4,945,914 A | 8/1990 | Allen | 128/653 R |
| 4,951,653 A | 8/1990 | Fry et al. | 128/24 A |
| 4,991,579 A | 2/1991 | Allen | 128/653 R |
| 5,016,639 A | 5/1991 | Allen | 128/653 R |
| 5,094,241 A | 3/1992 | Allen | 128/653.1 |
| 5,097,839 A | 3/1992 | Allen | 128/653.1 |
| 5,119,817 A | 6/1992 | Allen | 128/653.1 |
| 5,142,930 A | 9/1992 | Allen et al. | 74/469 |
| 5,178,164 A | 1/1993 | Allen | 128/898 |
| 5,186,174 A | 2/1993 | Schlondorff et al. | 128/653.1 |
| 5,197,488 A | 3/1993 | Kovacevic | |
| 5,198,877 A | 3/1993 | Schulz | 356/375 |
| 5,211,164 A | 5/1993 | Allen | 128/653.1 |
| 5,222,499 A | 6/1993 | Allen et al. | 128/653.1 |
| 5,230,338 A | 7/1993 | Allen et al. | 128/653 |

(Continued)

FOREIGN PATENT DOCUMENTS
DE          39 04 595          4/1990

(Continued)

OTHER PUBLICATIONS

International Search Report & Written Opinion for PCT/IB2005/004073 dated May 26, 2006.

(Continued)

*Primary Examiner* — Thomas C. Barrett
*Assistant Examiner* — Michael T Schaper
(74) *Attorney, Agent, or Firm* — McCracken & Frank LLP (57) ABSTRACT

A method of performing an arthroplasty of a ball and socket joint with a surgical navigation system includes the step of digitizing landmarks to provide geometrical parameters of the joint and a limb depending there from, including digitizing aspects of a socket region of the ball and socket joint. A range of motion parameter is determined. A soft tissue tension parameter is determined. A functional goal is computed based on landmark data, the range of motion parameter, the soft tissue tension parameter, and a database of potential implants. An optimal socket position is solved for to minimize impingement of potential implants. An implant is chosen based on the optimal socket position and the functional goal. The joint is prepared to receive the chosen implant. The chosen implant is installed into the joint.

21 Claims, 8 Drawing Sheets

U.S. PATENT DOCUMENTS

| | | | | |
|---|---|---|---|---|
| 5,309,101 | A | 5/1994 | Kim et al. | 324/309 |
| 5,383,454 | A | 1/1995 | Bucholz | 128/653.1 |
| 5,394,875 | A | 3/1995 | Lewis et al. | 128/660.09 |
| 5,397,329 | A | 3/1995 | Allen | 606/73 |
| 5,494,034 | A | 2/1996 | Schlondorff et al. | 128/653.1 |
| 5,515,160 | A | 5/1996 | Schulz et al. | 356/241 |
| 5,551,429 | A | 9/1996 | Fitzpatrick et al. | 128/653.1 |
| 5,575,794 | A | 11/1996 | Walus et al. | 606/116 |
| 5,590,215 | A | 12/1996 | Allen | 382/128 |
| 5,595,193 | A | 1/1997 | Walus et al. | 128/898 |
| 5,617,857 | A | 4/1997 | Chader et al. | 128/653.1 |
| 5,622,170 | A | 4/1997 | Schulz | 128/653.1 |
| 5,638,819 | A | 6/1997 | Manwaring et al. | 128/653.1 |
| 5,665,090 | A | 9/1997 | Rockwood et al. | 606/80 |
| 5,682,886 | A * | 11/1997 | Delp et al. | 600/407 |
| 5,690,635 | A | 11/1997 | Matsen, III et al. | |
| 5,695,501 | A | 12/1997 | Carol et al. | 606/130 |
| 5,704,897 | A | 1/1998 | Truppe | 600/117 |
| 5,711,299 | A | 1/1998 | Manwaring et al. | 128/653.1 |
| 5,730,130 | A | 3/1998 | Fitzpatrick et al. | 128/653.1 |
| 5,752,513 | A | 5/1998 | Acker et al. | 128/653.1 |
| RE35,816 | E | 6/1998 | Schulz | 356/376 |
| 5,769,789 | A | 6/1998 | Wang et al. | 600/414 |
| 5,797,924 | A | 8/1998 | Schulte et al. | 606/130 |
| 5,799,099 | A | 8/1998 | Wang et al. | 382/131 |
| 5,851,183 | A | 12/1998 | Bucholz | 600/425 |
| 5,871,445 | A | 2/1999 | Bucholz | 600/407 |
| 5,880,976 | A | 3/1999 | DiGioia III et al. | 703/7 |
| 5,891,034 | A | 4/1999 | Bucholz | 600/426 |
| 5,891,157 | A | 4/1999 | Day et al. | 606/130 |
| 5,907,395 | A | 5/1999 | Schulz et al. | 356/139.03 |
| 5,916,164 | A | 6/1999 | Fitzpatrick et al. | 600/426 |
| 5,921,992 | A | 7/1999 | Costales et al. | 606/130 |
| 5,954,648 | A | 9/1999 | Van Der Brug | 600/411 |
| 5,970,499 | A | 10/1999 | Smith et al. | 707/104 |
| 5,987,349 | A | 11/1999 | Schulz | 600/427 |
| 5,995,738 | A * | 11/1999 | DiGioia et al. | 703/11 |
| 6,073,044 | A | 6/2000 | Fitzpatrick et al. | 600/426 |
| 6,081,336 | A | 6/2000 | Messner et al. | 356/375 |
| 6,112,113 | A | 8/2000 | Van Der Brug et al. | 600/427 |
| 6,205,411 | B1 | 3/2001 | DiGioia, III et al. | 703/11 |
| 6,385,475 | B1 | 5/2002 | Cinquin et al. | |
| 6,430,434 | B1 | 8/2002 | Mittelstadt | 600/426 |
| 6,453,190 | B1 | 9/2002 | Acker et al. | 600/424 |
| 6,569,169 | B2 | 5/2003 | De La Barrera et al. | |
| 6,595,997 | B2 | 7/2003 | Axelson, Jr. et al. | |
| 6,676,706 | B1 | 1/2004 | Mears et al. | 623/22.4 |
| 6,695,850 | B2 | 2/2004 | Diaz | 606/91 |
| 6,702,821 | B2 | 3/2004 | Bonutti | |
| 6,711,431 | B2 | 3/2004 | Pratt et al. | 600/426 |
| 6,827,723 | B2 | 12/2004 | Carson | |
| 6,859,661 | B2 | 2/2005 | Tuke | |
| 6,877,239 | B2 | 4/2005 | Leitner et al. | |
| 7,275,218 | B2 | 9/2007 | Petrella et al. | |
| 7,427,200 | B2 | 9/2008 | Noble et al. | |
| 7,657,298 | B2 | 2/2010 | Moctezuma de la Barrera et al. | |
| 7,662,113 | B2 | 2/2010 | Pearl et al. | |
| 2001/0034530 | A1 | 10/2001 | Malackowski et al. | 606/130 |
| 2002/0133160 | A1 | 9/2002 | Axelson, Jr. et al. | |
| 2003/0153829 | A1 | 8/2003 | Sarin et al. | 600/426 |
| 2003/0153978 | A1 | 8/2003 | Whiteside | 623/20.21 |
| 2004/0034313 | A1 | 2/2004 | Leitner | 600/595 |
| 2004/0102866 | A1 | 5/2004 | Harris et al. | |
| 2004/0105086 | A1 | 6/2004 | Leitner et al. | 356/3 |
| 2004/0106861 | A1 | 6/2004 | Leitner | 600/407 |
| 2004/0106869 | A1 | 6/2004 | Tepper | 600/443 |
| 2004/0106916 | A1 | 6/2004 | Quaid et al. | |
| 2004/0117026 | A1 | 6/2004 | Tuma et al. | |
| 2004/0147927 | A1 | 7/2004 | Tsougarakis et al. | |
| 2004/0152972 | A1 | 8/2004 | Hunter | |
| 2004/0171924 | A1* | 9/2004 | Mire et al. | 600/407 |
| 2005/0065617 | A1 | 3/2005 | Moctezuma de la Barrera et al. | |
| 2005/0101966 | A1 | 5/2005 | Lavallee | |
| 2005/0113720 | A1 | 5/2005 | Cinquin et al. | |
| 2005/0119661 | A1 | 6/2005 | Hodgson et al. | |
| 2005/0203384 | A1 | 9/2005 | Sati et al. | |
| 2005/0234332 | A1 | 10/2005 | Murphy | |
| 2006/0235538 | A1 | 10/2006 | Rochetin et al. | |
| 2007/0179626 | A1 | 8/2007 | de la Barrera et al. | |

FOREIGN PATENT DOCUMENTS

| | | |
|---|---|---|
| EP | 0 326 768 | 8/1989 |
| EP | 0 705 075 B1 | 4/1999 |
| EP | 0 705 074 B1 | 5/2000 |
| EP | 1399707 | 3/2004 |
| EP | 1417941 | 5/2004 |
| JP | 3-267054 | 11/1991 |
| JP | 06-282889 | 10/1994 |
| JP | 06-282890 | 10/1994 |
| WO | WO 90/05494 | 5/1990 |
| WO | WO 00/39576 | 7/2000 |
| WO | WO 02/063236 | 8/2002 |
| WO | 03/041566 A2 | 5/2003 |
| WO | WO 03/041611 | 5/2003 |
| WO | 03/065949 A2 | 8/2003 |
| WO | WO 03/073951 | 9/2003 |
| WO | WO 03/079940 | 10/2003 |
| WO | WO 2004/014219 | 2/2004 |
| WO | WO 2004/030556 | 4/2004 |
| WO | WO 2004/030559 | 4/2004 |
| WO | 2005/072629 A1 | 8/2005 |

OTHER PUBLICATIONS

U.S. Appl. No. 10/655,922.

"Kinematik Approach to Hip Navigation," José Moctezuma Jul. 24, 2002 (4 pages).

"Surgical Steps for Computer Assisted Total Hip Arthroplasty," HipTrac V1.0 José Luis Moctezuma de la Barrera Jun. 4, 2000 (6 pages).

"Software Requirements Specification (SRS) Image Enhanced Knee Navigation, #1728," Richard Aschenbrenner Jun. 23, 2003 (46 pages).

"Rx90® Total Hip System Acetabular Series," Biomet Orthopedics, Inc. 2001 (11 pages).

"Radiographic and Non-Invasive Determination of the Hip Joint Center Location: Effect on Hip Joint Angles," R.N. Kirkwood et al. Oct. 16, 2003 (3 pages).

"Hip Joint Anatomy," http://vv.totaljoints.info/HIPJOINT_anatomydetails.htm Oct. 7, 2003 (3 pages).

"Virtual Planning of Hip Operations and Individual Adaption of Endoprostheses in Orthopaedic Surgery," H. Handels et al. (12 pages).

"Inclination," http://www.gentili.net/thr/inclinat.htm Oct. 16, 2003 (1 page).

"Hip: Functional Method," http://kwon3d.com/manuals/kwon3d30/modeling/hip_func.html Oct. 16, 2003 (4 pages).

Web page from http://www.totaljoints.info/NORMALHIPJOINTIMAGE.jpg Oct. 7, 2003 (1 page).

Web page from http://www.totaljoints.info/REPLACEDHIPJOINTIMAGE.jpg Oct. 7, 2003 (1 page).

Web page from http://www.totaljoints.info/ANT_approach2.jpg Oct. 7, 2003 (1 page).

Web page from http://www.totaljoints.info/POST_approach2.jpg Oct. 7, 2003 (1 page).

Birkfellner et al., "Evaluation and Detection of Systematic Distortions in DC-pulsed Electromagnetic Position Sensing Devices," *Elsevier Science B.V.*, 1998, pp. 927-928.

Birkfellner et al., "Systematic Distortions in Magnetic Position Digitizers," *Med. Phys.* 25 (11), pp. 2242-2248 (Nov. 1998).

Livingston et al., "Magnetic Tracker Calibration for Improved Augmented Reality Registration," *Presence*, vol. 6, No. 5, pp. 532-546 (Oct. 1997).

State et al., "Superior Augmented Reality Registration by Integrating Landmark Tracking and Magnetic Tracking," Proceedings of SIGGRAPH 96 (New Orleans, LA, Aug. 4-9, 1996). In *Computer Graphics* Proceedings, Annual Conference Series, pp. 429-438.

Birkfellner et al., "Calibration of Tracking Systems in a Surgical Environment," *IEEE Tansactions on Medical Imaging*, Nov. 17, 1998, pp. 1-6.

Birkfellner et al., "Evaluation of Magnetic Position Digitizers for Computer Assisted Surgery," *Comput. Aided Surg.* 2(3/4), 225 (1997).

International Search Report and Written Opinion dated Aug. 15, 2001, Int'l. Appl. No. PCT/US01/02166.

Applied Neurophysiology, Journal of Stereotactic and Functional Neurosurgery, Proceedings of the Meeting of the American Society for Stereotactic and Functional Neurosurgery, Montreal, Quebec, (Jun. 3-6, 1987) Jan. 1998.

Stereotactic & Functional Neurosurgery vol. 53, No. 3, (1989) pp. 197-201.

Journal of Ultrasound in Medicine vol. 9, No. 9, (Sep. 1990), pp. 525-532.

Ultrasound in Neurosurgery J.M. Rubin et al. ISBN: 0881675490, pp. 47-58.

Stereotactic & Functional Neurosurgery vol. 54-55, (1990), pp. 419, 422, 423, 471-476, 482-487, 488-492, 493-496, 497, 498, 500.

British Journal of Neurosurgery vol. 4, No. 3, (1990), pp. 193-197.

IEEE Computer Graphics & Applications vol. 3, No. 10, (May 1990), pp. 43-51.

Journal of Neurosurgery vol. 72, No. 2, (Feb. 1990), pp. 355a.

IEEE Engineering in Medicine & Biology Society—Proceedings of 11th Annual International Conference, (1989), pp. 925, 926-929.

British Journal of Neurosurgery vol. 3, No. 5, (1989), pp. 561-568, 569-574.

British Journal of Neurosurgery vol. 3, No. 3, (1989), pp. 327-331.

Acta Neurochirurgica Supplementum 46, (1989), pp. 112-114.

Journal of Neurosurgery vol. 65, No. 4, (Oct. 1986), pp. 550-554, 557-559.

Journal of Neurosurgery vol. 57, No. 2, (Aug. 1982), pp. 157-163.

Neurosurgery vol. 10, No. 5, (May 1982), pp. 580-586.

Neurosurgery vol. 10, (Mar. 1982), pp. 375-379.

Guided Brain Operations E.A. Spiegel ISBN: 3805534515, (1982), pp. 23, 25, 28.

American Journal of Neuroradiology vol. 2, No. 2 (Mar./Apr. 1981), pp. 181-184.

Neurosurgery vol. 8, No. 1 (Jan. 1981), pp. 72-82.

Surgical Neurology vol. 14, No. 6, (Dec. 1980), pp. 451-464.

Investigative Radiology vol. 15, No. 4, (Jul./Aug. 80), pp. 308-312.

Applied Neurophysiology vol. 43, No. 3-5, (1980), pp. 170-171, 172-173, 174-175.

Neurosurgery vol. 3, No. 2, (Sep./Oct. 1978), pp. 157-161.

U.S. Appl. No. 10/798,614.

* cited by examiner

SYSTEM AND METHOD FOR PERFORMING ARTHROPLASTY OF A JOINT AND TRACKING A PLUMB LINE PLANE

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to orthopedic surgery, and more particularly to a system and method for performing replacement or arthroplasty of a ball and socket joint.

2. Description of the Background of the Invention

There are two major types of ball and socket joints in human anatomy, two hip joints and two shoulder joints. There are a number of surgical approaches to repair of these ball and socket joints. For the hip joint, total hip arthroplasty (THA) or replacement surgery is used to provide increased mobility to patients who have significant problems with one or both of their hip joints, including injury, arthritis, bone degeneration, cartilage damage or loss, and the like. The classic THA surgery involves the dislocation of the hip joint following an incision to access the joint. Following dislocation of the joint, the femoral head is removed from the femur by cutting the femur through the femoral neck. The hip socket or acetabulum is then reamed out using a power tool and reaming attachment to remove the cartilage remaining within the acetabulum and to prepare the acetabulum to accept the acetabular implant component or cup. Typically, the reamer attachment is sized to prepare the acetabulum to accept a particular type of implant cup or component. The implant cup is held in place by cement, special screws and or by a mesh that accepts bone growth to firmly affix the cup to the pelvis.

The femur is then prepared by reaming the femoral canal using specialized rasps or similar instruments to shape the femoral canal to accept the fermoral stem implant. The femoral stem implant is then placed in the reamed out canal and affixed in place in a manner similar to the acetabular cup. The last step in the classic procedure is to attach a metal ball to the stem to act as the hip pivot point within the cup.

For the shoulder joint, total replacement surgery is less common, and typical replacement surgery may only replace the ball of the humerus and often does not involve any cup implant. In this case, the surgery typically will replace the ball of the humerus and sometimes make various levels of modification to the surface of the glenoid socket.

Because the relative size and configuration of the implants can affect the length and offset of the leg or arm, care must be taken in the choice of the particular implants chosen. In addition, care must be taken in reaming out the socket, whether the glenoid or the acetabulum, at an appropriate position/orientation to achieve desired kinematics. Often, prior to affixing the permanent implants in place, trial implants are placed in position to assist the surgeon to gauge the impact of the replacement surgery on the patient's mobility, range of motion, and quality of life. These issues include for the hip joint, making sure the leg length closely matches the length of the non-operative leg, making sure the offset of the replacement hip joint is satisfactory so that the appearance of the leg matches the non-operative leg, and making sure the replacement joint is sufficiently stable so that normal activity by the patient will not cause the hip to dislocate or cause the leg not to be able to properly support the patient during walking and other normal routine activities. For the shoulder, the length of the arm, the offset, and range of motion of the arm and shoulder must match the non-operative arm and shoulder and the operative shoulder must not dislocate under normal activity. One concern with the use of trial implants is that these trial devices are used after all preparation of the bone has taken place. If the trial indicates that the depth of the preparation is too great the surgeon is left with using implants of a different configuration to attempt to address the situation. This requires having a greater inventory of implants on hand before the surgery begins in order to address contingencies that may occur.

In addition, the classic surgical technique presents the surgeon with a number of other challenges. The use of surgical navigation and appropriate pre-surgical planning can minimize these challenges, but even with the use of these tools, care must be taken to insure appropriate modifications to the bone are made during the surgery. For instance with hip replacement surgery, it is necessary to prepare the acetabulum to a suitable depth to accept a certain acetabular implant cup, but at the same time avoid violating or compromising the medial wall of the acetabulum. At the same time, it is necessary to make sure that the acetabulum is prepared to properly accept the implant cup. If the cup does not sit well within the prepared acetabulum, for instance, if the prepared acetabulum is deeper than the depth of the cup or the cup can not be placed sufficiently deep within the acetabulum, the cup will either become loose over time or the pelvic structure may be damaged as the cup is impacted into place. There can be similar concerns for the shoulder if the glenoid is resurfaced or modified.

In addition to concerns relating to limb length and offset mentioned above, many surgeons may rely on mechanical guides to orient implants in position relative to the patient's anatomy, which can result in imprecise and less than optimal joint function. Lastly, the surgeon must rely on experience to assess the finished range of motion and stability of the completed joint and the consequent potential for the joint to dislocate under normal everyday activities.

SUMMARY OF THE INVENTION

One embodiment of the present invention relates to a method of performing an arthroplasty of a stem-ball and socket joint with a surgical navigation system. The method comprises the steps of digitizing landmarks to provide geometrical parameters of the joint and a limb depending there from, including digitizing aspects of a socket region and the stem of the limb; determining a range of motion parameter; and determining a soft tissue tension parameter. The method further includes the step of computing a functional goal based on landmark data, the range of motion parameter, the soft tissue tension parameter, and a database of potential implants. Next, the method includes solving for an optimal socket orientation to minimize impingement taking into account stability constraints based on an identified center of rotation of the socket; choosing an implant components combination and positioning to match the functional goals; solving for an optimal socket position to minimize impingement taking into account stability constraints based on an identified stem position and the identified center of rotation of the socket; and solving for an optimal components combination and positioning to match the functional goals based on the optimal socket position; In addition, the method also has the steps of solving for an optimal components combination and orientation to match the functional goals based on the optimal socket position and the identified stem position; choosing a final components combination and a final orientation of the components to match the functional goals; preparing of the joint to receive the final implant components; and installing the final implant components into the joint.

A further embodiment of the present invention is directed to a method of selecting and positioning an implant into a ball and socket joint by taking into account both geometrical parameters and soft tissue tension parameters with a surgical navigation system. The method comprises the steps of digitizing geometrical parameters and range of motion data; measuring a soft tissue tension parameter; and selecting a first socket position that provides adequate stability and minimal potential for impingement. The method further includes the steps of establishing an acceptable tolerance range from the first socket position with regard to limb length, distal/proximal displacement, and lateral/medial displacement; selecting an initial implant combination of components; and calculating and graphically displaying attributes of the initial implant combination of components and a position of the initial implant combination of components relative to a range of additional potential attributes for additional potential implant combinations of components and for additional positions of the initial combination of components. Lastly, the method includes the step of modifying the initial implant combination of components and the initial position of the initial combination of components to arrive at a final implant combination of components and a final position of the final combination of components for optimal functional properties of the joint while staying within the tolerance range.

A still further embodiment of the present invention is directed to a method of performing an arthroplasty of a joint with a surgical navigation system. The method comprises the steps of establishing and tracking a functional plane of the joint relative to a predetermined at rest position; and establishing and tracking a plumb line relative to the functional plane. The method further includes the steps of preparing the joint to receive implant components; choosing implant components that minimize impingement and maximize range of motion; and inserting the chosen implant components into the prepared joint.

Other aspects and advantages of the present invention will become apparent upon consideration of the following detailed description.

DETAILED DESCRIPTION OF THE PREFERRED EMBODIMENTS

Figure 1:
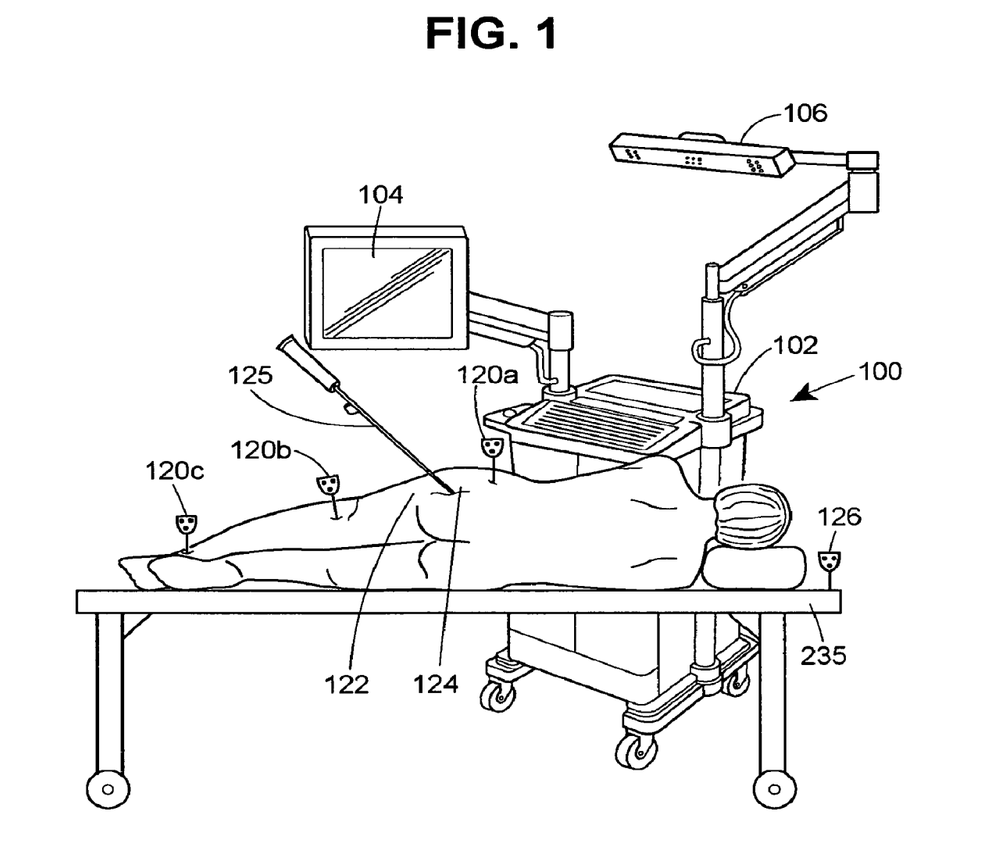
FIG. 1 is a schematic view of a surgical navigation system useful in the method of the present invention.

FIG. 1 illustrates a surgical navigation system 100, which includes a personal computer 102 having a CPU (not shown), internal memory (not shown), storage capacity (not shown), a monitor 104, and a camera array 106. The elements of the surgical navigation system 100 are well known to those of skill in the art and there are many commercially available systems that can be adapted for use according to the methods of the present invention, such as the surgical navigation system as disclosed in published U.S. patent application 2001/0034530, the disclosure of which is incorporated by reference. A system and methods for performing a ball and socket joint arthroplasty with the aid of a surgical navigation system is generally discussed in commonly assigned U.S. patent application Ser. No. 10/655,922 filed Sep. 5, 2003, also incorporated herein by reference.

Functional driven positioning of one or more implant components takes into account range of motion and muscular tension to establish the orientation and position of the implants. In a conventional surgical procedure, orientation and positioning of an implant component may involve adhering to standardized position values that are not patient-specific and hence may result in less than optimal positioning and orientation from a functional standpoint. For example, in a conventional hip replacement procedure, a surgeon may adhere to a standard value of 20° of anteversion and 45° of inclination relative to the anatomical frontal plane for a cup implant as is well known in the art. Available medical literature shows that the anatomical references used during a surgical procedure for these fixed average values of 20° and 45° may be somewhat arbitrary because these values are averages and may not correspond to the optimal function of the joint. For example, for a patient having a tilted pelvis when standing upright, the conventional approach would dictate an amount of cup inclination and anteversion based on the frontal plane of the pelvis as measured while the patient is lying down without taking into account that when the patient stands the pelvis is flexed.

Figure 2:
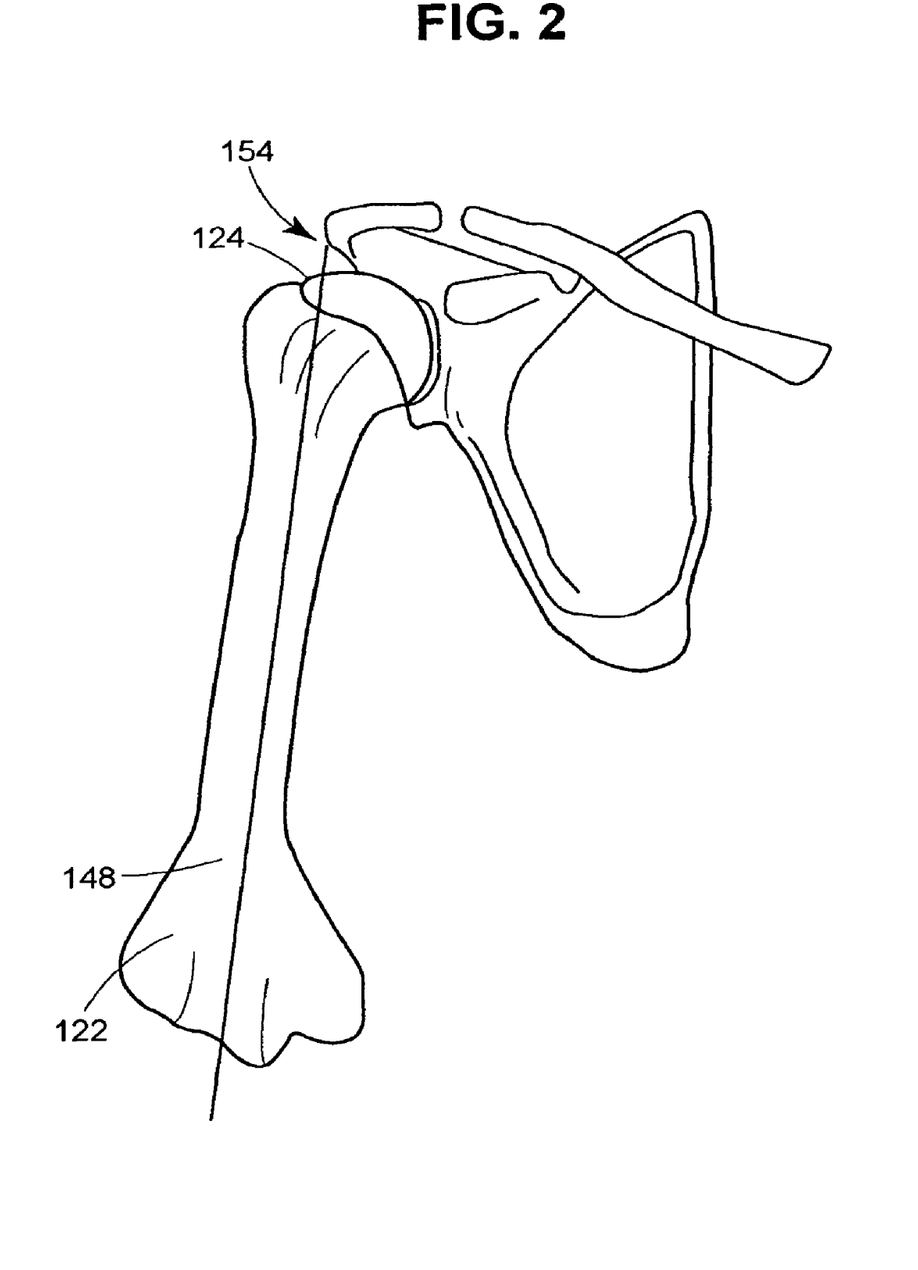
FIG. 2 an anatomical view of a shoulder.

To achieve the optimum results in a joint arthroplasty procedure for a ball and socket joint, there are several interrelated goals the surgeon strives for. The first goal is sufficient stability of the socket. For example in a hip procedure, an acetabular cup implant must be well seated in the bone and positioned and oriented appropriately to withstand years of loading. The cup implant must not be bored so deeply into the pelvic wall to compromise the structural integrity of same. Alternatively, in a shoulder procedure, the glenoid 154 (shoulder socket shown in FIG. 2) if machined or reamed to accommodate a shoulder implant component, must not be overly reamed in a manner that would compromise the structural integrity of the glenoid. In a shoulder procedure, which typically does not employ a cup or socket implant, the glenoid 154 must be machined or reamed as necessary to create a surface suitable for accommodating a replacement ball implant attached to the humerus 148 wherein the ball implant interacts with the surface. In a manner analogous to a hip procedure, the preparation of the glenoid 154 affects the ultimate shoulder joint position, and thus, affects not only the range of motion of the shoulder joint but also has at least some affect on the arm length and/or medial-lateral arm position.

The second goal is minimal tendency or risk of impingement/dislocation. For example, it is desirable in a hip procedure to position and orient a cup implant such that a neck implant does not impinge against a rim of the cup implant during the expected normal movement of the limb, potentially causing the ball of the neck implant (which ball fits within the cup implant) to dislocate (i.e., pop out) from the cup implant during expected normal movement of the limb. These first two goals of (1) stability and (2) minimal risk of impingement/dislocation are typically the most important considerations for the socket because insufficient stability and a tendency for impingement and dislocation could severely impair the function of the joint.

There are additional goals or factors to consider, discussed hereinbelow, that are also affected by the orientation and positioning of the socket or socket implant. Once the surgeon has determined a first position and orientation of the socket/socket implant that would be sufficient from a stability and impingement/dislocation standpoint, the surgeon may consider how much she may reasonably deviate from this first socket position/orientation to achieve the additional goals. The surgeon may then fine-tune or tweak the positioning and orientation from the first position/orientation to achieve or at least approach the additional goals.

The additional goals include a third goal of arriving at a socket position and orientation that results in matching the lateral-medial displacement of the operative limb to the non-operative limb (i.e., the contralateral side) or at least approaching lateral-medial displacement similar to the contralateral side. A fourth goal includes positioning/orienting the socket such that the distal-proximal placement of the operative limb matches or approaches the contralateral side. A fifth goal is to match the length of the operative limb to the contralateral side. A sixth goal includes matching (or approaching) the center of rotation of the contralateral side. It should be noted that matching the center of rotation to the contralateral side may be considered less important than matching the leg length or other of the goals. For example, the surgeon may establish an arbitrary center of rotation/first socket position that ignores precisely matching the socket position of the contralateral side but provides optimal stability for the socket. As discussed hereinbelow, the surgeon may then use left over degrees of freedom to fine-tune from the first socket position to achieve an optimal function and desired limb length A seventh goal is matching the kinematics of contralateral side (i.e., similar range of motion). However, depending on the anatomical constraints of the patient matching the kinematics may be less important than other of the goals. As should be evident from the "approaching" language above, the surgeon may have to compromise slightly or substantially on one or more of these additional goals in order to arrive at position and orientation of the socket that is optimal regarding the majority of the first through seventh goals. The degree to which one or more of the seven goals need be compromised may depend in large part on the anatomical constraints of the patient.

Besides socket positioning/orienting, the selection of implant(s) affects the aforementioned goals. The particular dimensions (i.e., size) and geometry (e.g., angles) of the selected implant(s) are an important consideration relative to achieving one or more of the first through seventh goals. For example, in a hip procedure, a particular implant may have a neck length longer or shorter than other available implants. The particular length of the neck affects the lateral-medial and distal-proximal displacement of the operative femur relative to the contralateral side. In addition, the particular angle the neck makes with a femoral stem implant affects the lateral-medial and distal-proximal displacements.

Referring to FIG. 1, with a surgical navigation system 100 a surgeon applies suitable markers 120a, 120b, 120c secured in fixed relation to appropriate anatomical landmarks, in a manner well known in the art, to input geometrical parameters of a ball and socket joint 122 and a limb 124 depending therefrom into the system 100, and the surgeon may also digitize various positions of a movable probe 125 as is also well known in the art. In addition, one or more stationary markers 126 are typically digitized. The surgeon also digitizes range of motion data by moving the limb 122 about the joint 124 and measures soft tissue tension data with an appropriate force sensor as discussed hereinbelow. The system 100 transforms these data to calculate a first socket position as well as a particular implant or combination of implant components that is determined optimal with regard to the first and second goals as well as all or any of the third through seventh goals. At this point the system 100 will indicate the best combination of implant components to achieve the desired functional result. As there is a finite number of implant component combinations, the system 100 will indicate that combination of implant components that best achieve the optimum result.

The surgeon may then establish an acceptable tolerance range from the first socket position/orientation within which the surgeon feels comfortable adjusting from the first socket position/orientation. Referring to FIG. 5, the system 100 preferably displays a graphical representation 130, which includes a first axis 133 for anteversion and a second axis 136 for inclination. A dot 137 represents the present socket position relative to inclination and anteversion. Function curves 138a-138f represent transformations of all available geometrical, range of motion, and soft tissue tension data relative to varying values of inclination and anteversion and such transformations are computed by the system with an appropriate algorithm. The system 100 also determines a first implant component(s) with regard to the first and second goals and perhaps one or more of the third through seventh goals. In this regard, the system 100 utilizes an implant database 143 (FIG. 4A) having the geometrical properties of each potential implant for computing the optimal first implant. The system 100 and methodology disclosed herein takes into account all of the above parameters at the same time. The algorithm used by the system 100 uses the database 143 with all of the implants components and optimizes the above parameters by choosing an appropriate combination of components and respective alignments (e.g., head offset, neck angle, cup orientation) therefor. The implant components in the database 143 can be complete sets of implants of varying sizes as well as modular implants that can be combined by the surgeon to produce a more customizable implant. The modular implants include separate and interchangeable stems, necks and balls or heads. The system 100 then indicates on the display 104, the particular optimized implant(s) and also displays the graph 130 of the various function curves 138a-138f for the particular optimized implant. As part of the optimization algorithm, some parameters are binary, e.g., no dislocation, while other parameters may have a small tolerance range such as a leg length tolerance range of +/−5 mm relative to the contralateral side. Any two points on any of the curves 138a-138f are equivalent from a functional standpoint of the joint 124. For example, on curve 138d, points 140 and 141 produce an equivalent functional outcome in terms of range of motion and tension despite having different values of inclination and anteversion. In addition, the system 100 can also display alternate graphs showing the results for other choices of implant components, such as the neighboring sizes to the determined optimum solution or a different implant family using an alternative implant design. A surgeon may determine a minimum anteversion value 143 and a maximum anteversion value 146 with regard to the first and second goals of stability and non-impingement/dislocation. Similarly, the surgeon may also establish minimum and maximum values 148 and 150 between which the surgeon may manipulate from the position 137 to improve joint function without compromising the first and second goals. Generally, in the graph 130, function improves from the curve 138a toward the curve 138f. Therefore, the surgeon may adjust inclination and anteversion from the position 137 to a position 152 of the curve 138c rather than a position 154 of the curve 138b, because the curve 138c yields a better functional outcome than the curve 138b.

The soft tissue tension data are collected by the system by any suitable pressure sensor built into the acetabular cup, or into the femoral head or neck implant of the trial implants. The pressure sensors are conventional strain gauges that are built into the trial components. These trial components enable the surgeon to test the configuration to confirm that the optimum solution is in fact optimal for the patient. The pressure values can be transmitted to the system 100 wirelessly and can be related to the respective limb position. As part of the process of gathering soft tissue tension data, the surgeon may use trial implant components that have not only the above pressure sensors but motorized parts that adjust one or more implant features such as neck offset/length or neck angle, and the system 100 could calculate soft tissue tension parameters relative to various values of neck length or neck offset angle. During movement of the limb 122, the system is provided with lift-off data upon the system detecting displacement of the center of rotation of the joint 124 as is well known in the art.

The performance of trials with a pressure sensor may be conducted after the system 100 determines the first socket position/first implant(s). For example, the surgeon could manipulate the neck angle and/or neck length and display a further function graph similar or identical to the graph 130 of FIG. 5. The change in neck length/neck angle provides further force data for further transformations for further function curves similar to the curves 138a-138f allowing the surgeon to fine-tune from the first position to improve function relative to the third through seventh goals.

A typical scenario would be as follows. The surgeon captures preoperative range of motion. The surgeon prepares the acetabulum or glenoid and places a swivel trial. The surgeon reams a trial broach into the femur. According to a first option or procedure, the surgeon reams to a final position in terms of depth and anteversion, thus decreasing the degrees of freedom for later optimization. The surgeon next places a trial neck and head and performs a further range of motion. The system 100 then derives an optimal neck angle, head offset, anteversion, and inclination of cup.

According to a second option or procedure, the surgeon places a preliminary broach in place rather than reaming to the final position in terms of depth and anteversion. According to this second option or procedure, maximum degrees of freedom are provided because the position is not final. The surgeon next tests the trial neck and head and performs a range of motion analysis therefor. The system 100 derives an optimal stem anteversion and all of the above. The surgeon next verifies the proposed femoral components. Verification includes the assembly of the selected components in situ or if a automatically adjustable device is in place then the degrees of freedom of the device are adjusted accordingly. The trial neck with proposed angle and head with proposed offset are mounted manually. The surgeon performs one or more smart trials, utilizing motorized implant components as discussed above to adjust the proposed neck angle, offset, and anteversion in situ. Additional force data is collected, allowing further transformations and further graphical displays such as the graphical display 130 by the system 100, and thus allowing the surgeon to fine-tune the implant component(s) geometry. The trial implant could include an extensible femoral neck and a force sensor that communicates force data to the system so that during registration of the second movement the surgeon can assess the affect of soft tissue tension on the neck length. The surgeon may vary the neck length in the performance of movement analyses and transmit force data for various neck lengths. Based on the acquired force data, the surgeon can use the system to determine an optimal neck length that provides suitable tension while also resulting in an offset that is cosmetically acceptable (i.e., within appropriate geometrical parameters). Finally, the surgeon navigates final components to the optimized positions. Depending on surgeon preferences, the above options or procedures can differ in order and degrees of freedom available for optimization.

Sometimes initial kinematics of the patient are taken into account. They can be used as a reference to document the improvement of the surgical measure. Sometimes, when the disease permits, it will be desirable to reestablish center of rotation, range of motion and soft tissue tension. The most common situation though will be to try to optimize the ipsilateral side regardless of the initial state such that the surgeon establishes an arbitrary first socket position/center of rotation as discussed above. In cases where reestablishment of the original center of rotation is desired, a first kinematic analysis is performed by moving the contralateral limb about the joint to obtain first kinematic data and the operative limb 124 is moved about the joint 122 to obtain second kinematic data that is compared to the first kinematic data.

Figure 3:
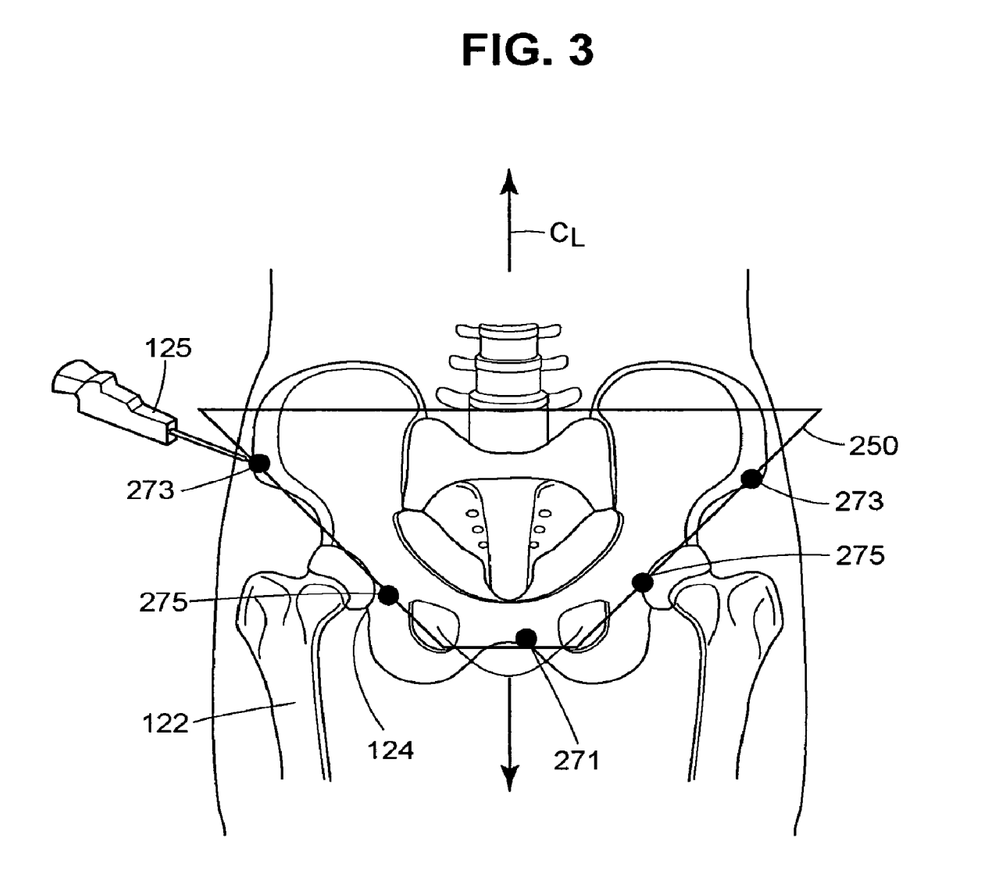
FIG. 3 is an anatomical view of a pelvis and a frontal pelvic plane.
Figure 4A:
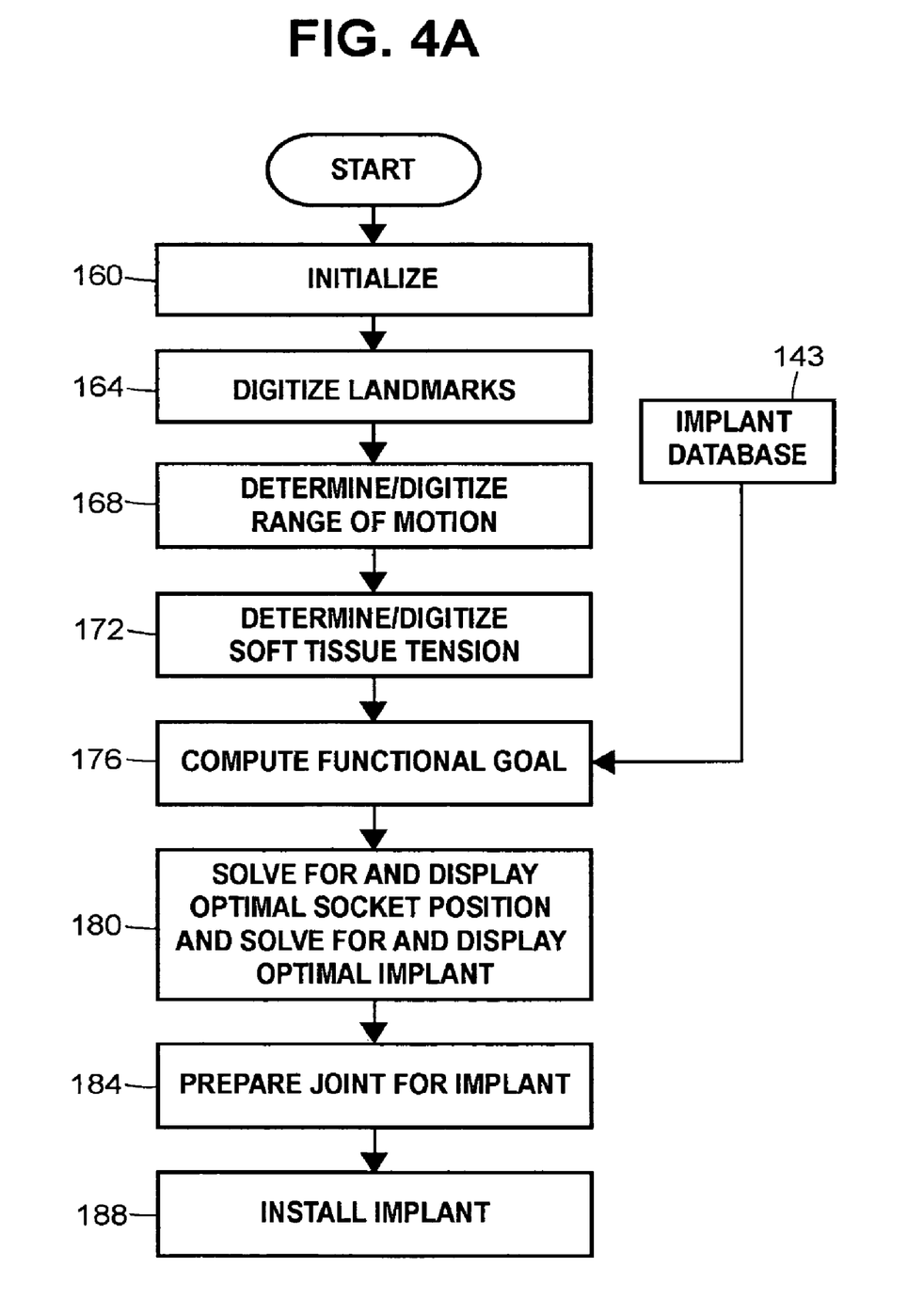
FIG. 4A is a flow diagram of one embodiment according to the disclosure.
Figure 5:
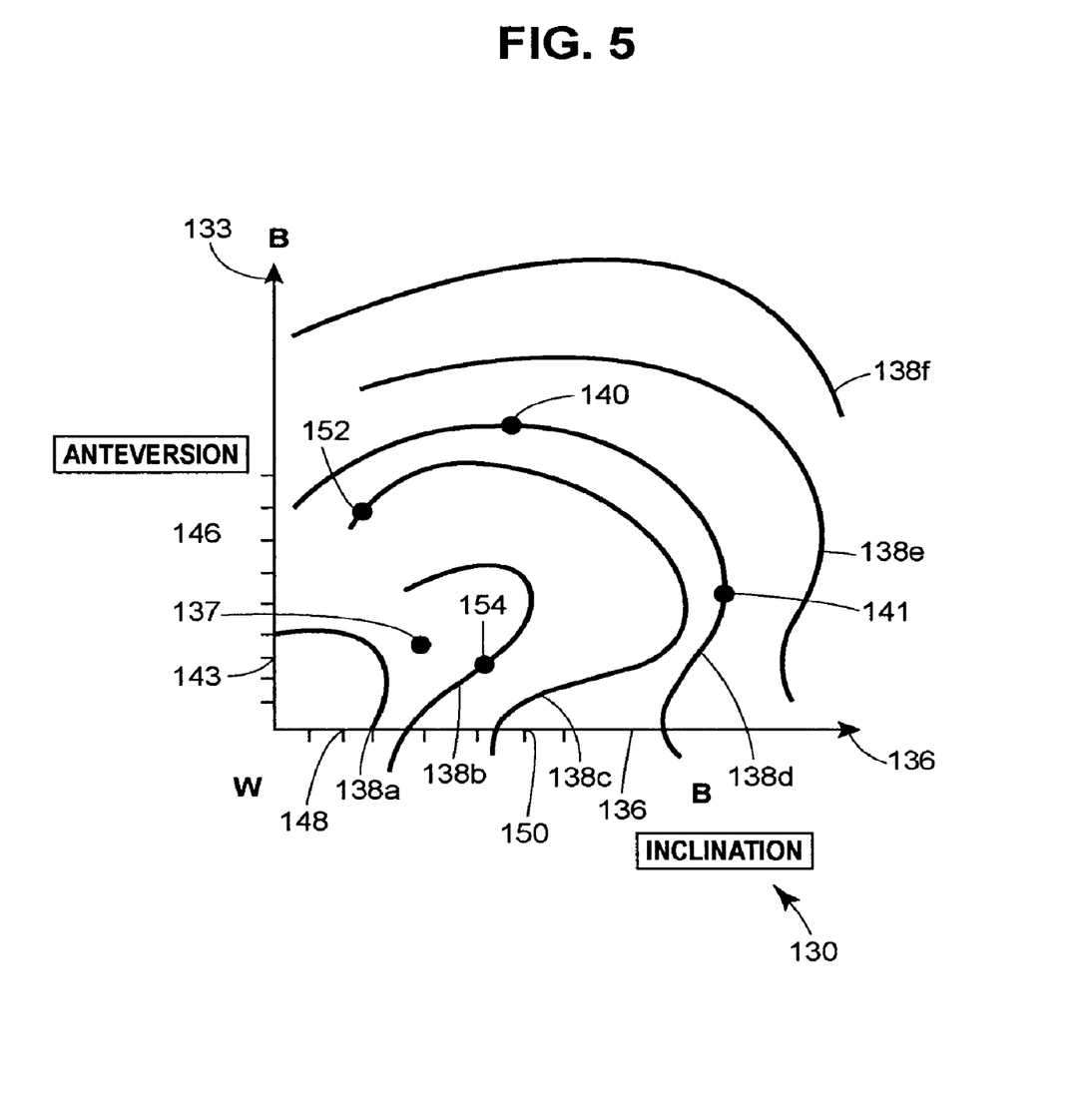
FIG. 5 is a graphical display of functional yield curves relative to anteversion and inclination axes.

Referring to FIG. 4A, a block 160 initializes the system 100 and allows input of patient biographical information and tests whether the markers 120a-120c and the probe 125 are within the viewing volume of the camera array 106. A block 164 receives input from each of the markers for determining geometrical parameters, and a block 168 calculates range of motion by digitizing the markers 120a-120c following or during movement of the limb 122 about the joint 124 within the viewing volume. While the limb is moved through a full range of motion the limb location is repeatedly digitized at various locations in a known manner. The surgeon typically assesses extreme positions such as maximum flexion, maximum extension, maximum internal rotation, maximum external rotation, maximum abduction, and maximum adduction. The surgeon typically also digitizes moderate positions of each of these. The surgeon need not digitize a frontal plane such as the anatomical frontal pelvic plane 250 based upon the suspensory ligament 271, a left and right ASIS 273 and pubic tubercles 275 (seen in FIG. 3) because the first kinematic data, comprising geometrical parameters and range of motion data, is sufficient to assess the kinematics of the joint and solve for an optimal socket position and in fact produces a better result. The functional frontal planes that are used in the system and method of the present invention replicates the pelvic position in certain poses, e.g. standing or sitting, relative to gravity. These functional frontal planes are then a patient specific reference to implant positioning in a static scenario. These are more meaningful to fulfillment of daily activities than an arbitrarily defined anatomical frontal plane. A block 172 determines the soft tissue tension parameter of the joint 124 via wireless receipt of force data as described above. A block 176 computes a functional goal by accessing the implant database 143 and performing an optimization algorithm that chooses the best implant(s) based on the geometrical parameters, the soft tissue tension data, the first and second goals, and one or more of the third through seventh goals. A block 180 displays the optimal socket position and the optimal implant(s). In a block 184, the surgeon prepares the joint 124 for receipt of an implant, whether a trial implant or a final implant. Reaming/preparation of the joint 124 could be guided by the system 100 as known in the art such as by guiding a suitable reamer (not shown but well known) having suitable active or passive tracking markers thereon. Finally, in a block 188 the implant(s) is installed into the joint 124. It should be noted that in between the blocks 184 and 188 the block 172 could be repeated perhaps with the performance of a smart trial as discussed above to fine-tune the socket positioning and implant selection. It should be further noted that the blocks 168, 172 could be either combined or separate as shown.

Figure 4B:
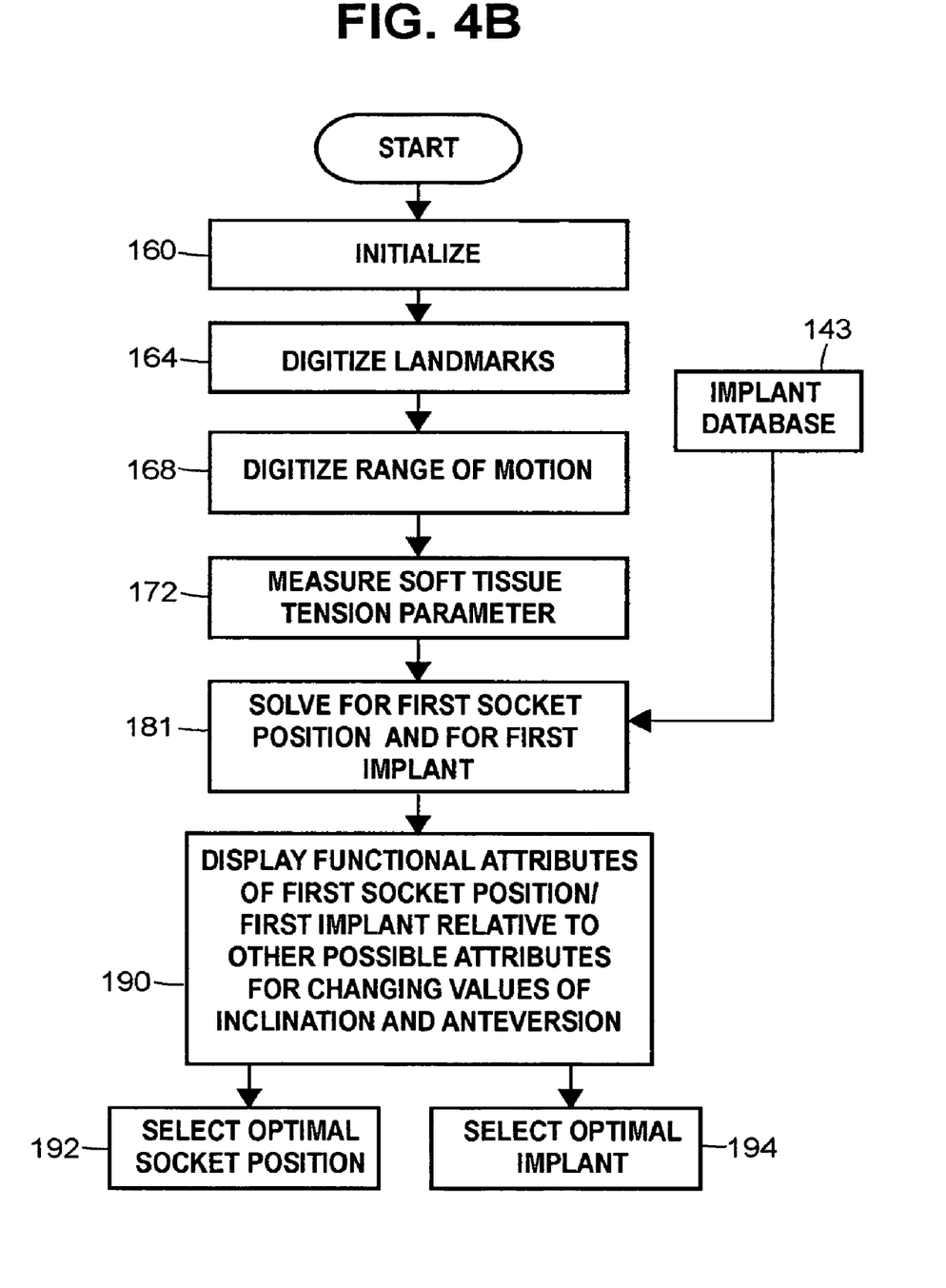
FIG. 4B is a flow diagram of a second embodiment according to the disclosure.

Referring to FIG. 4B, a block 181 similar or identical to the block 180 solves for a first socket position and a first implant by optimizing data obtained from the blocks 160, 164, 168, 172, and 143. A block 190 displays the functional attributes of the first socket position/first implant relative to varying values of inclination and anteversion. For example, the block 190 could display the point 137 (FIG. 5) relative to the various curves 138a-138f. Finally, in blocks 192, 194 the optimal socket position and optimal implant, respectively, are selected. A smart trial, discussed above, could optionally be performed in between the block 190 and the blocks 192, 194 to obtain further optimization data.

Figure 6:
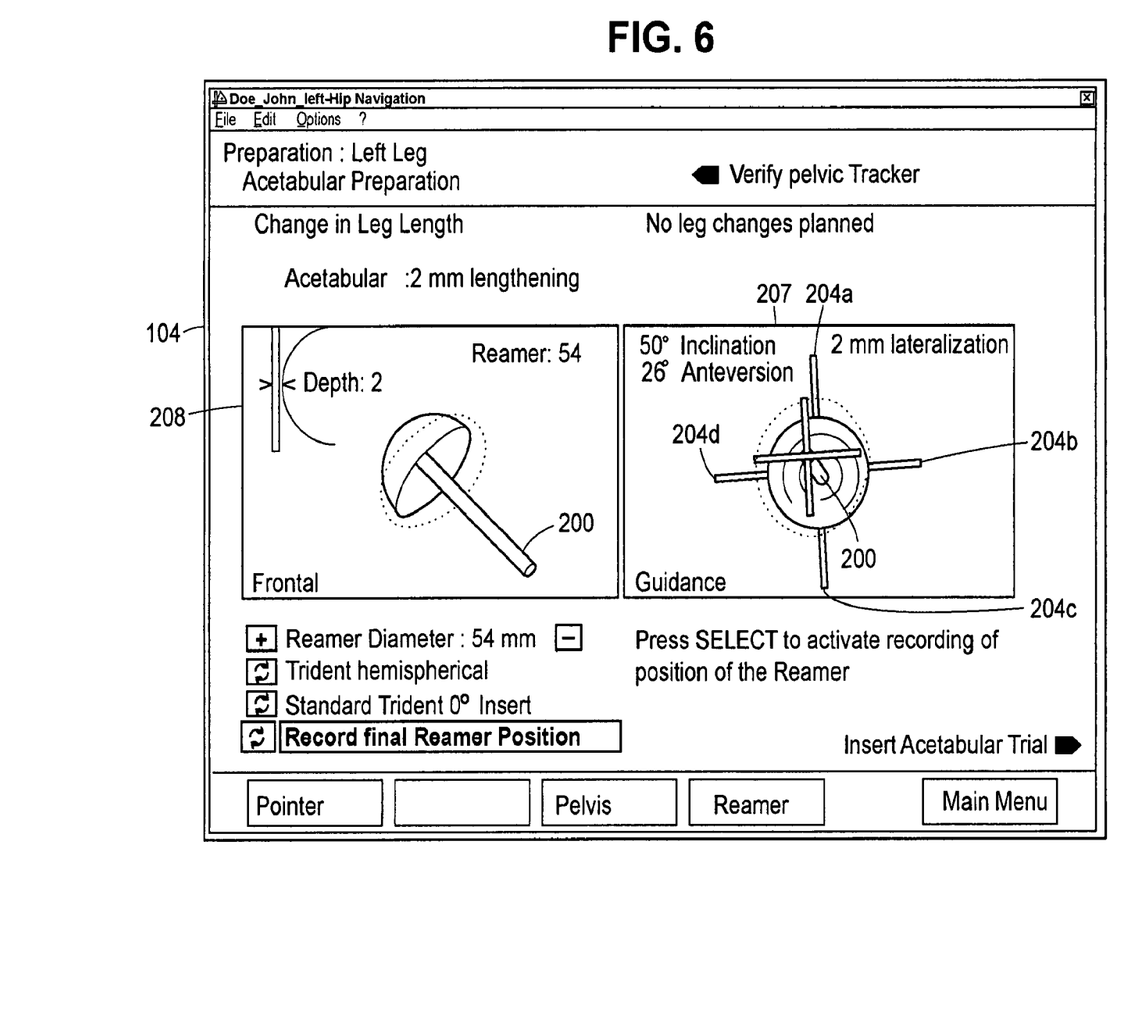
FIG. 6 is a diagrammatic view of a display screen that guides navigation of a reamer.

Referring to FIG. 6, navigation of a reaming tool 200 may be accomplished by providing suitable indicia on the display 104 (see also FIG. 1). For example, one or more guide lines 204a-204d that reflect the desired reaming location displayed on the display 104. The position of the reaming tool 200 is displayed in real-time by any suitable indicia such as a crucible 207, and the crucible 207 is displayed relative to the guide lines 186. The indicia could further include a guide line 208 that reflects the maximum reaming depth. It should be noted that the surgeon may perform one or more virtual trials (as discussed in commonly assigned U.S. application Ser. No. 10/655,922) for various hypothetical positions of a hypothetical implant in order to test the surgeon's estimated position prior to any reaming. The system 100 would display the expected kinematic outcome of such virtual trial(s) to assess the surgeon's estimated optimal socket position. The surgeon may even perform further virtual trials utilizing different hypothetical implants having different dimensions. Through a process of trial and error, the surgeon could solve for the optimal socket position, and once an optimal socket position has been determined the system displays suitable indicia such as the guide lines 204a and 204b (FIG. 6) to guide preparation of the joint.

Figure 7:
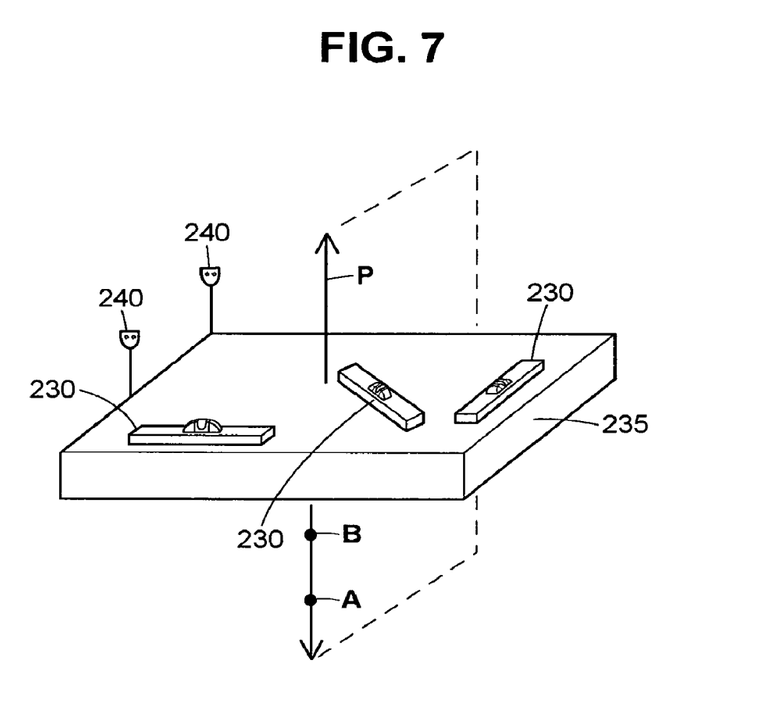
FIG. 7 is a diagrammatic view of an operating table.

Referring to FIG. 7, the surgeon may optionally establish and track a gravitational or plumb line plane P relative to an anatomical plane of the patient during the data collection described in connection with the blocks 160, 164, 168, and 172 described above. In a hip procedure, the plumb line plane P allows the system to assess the position of the pelvis relative to gravity. In this regard, optimal socket positioning is generally assessed with the pelvis in a neutral stance wherein the functional frontal plane of the pelvis offset relative to the plumb line plane P when the patient is lying down. The angle of the offset varies not only between genders but also depending on lifestyle, age, races, etc. It typically ranges from −10 to +10 degrees but can also lie outside this range. Tracking the plumb line plane P allows the system to guide joint preparation or implant navigation relative to the plumb line plane P or preferably relative to an established functional frontal plane, without having data obscured by imprecision caused by an non-level table exerting a gravitational affect on the pelvis or having the data obscured by shifting of the patient's pelvis during a procedure.

Figure 8A:
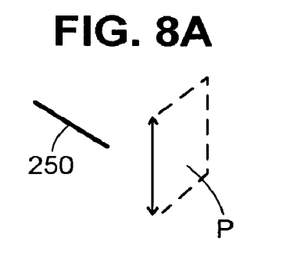
FIGS. 8A-8C illustrate a position of an anatomical plane relative to a plumb line plane.
Figure 8B:
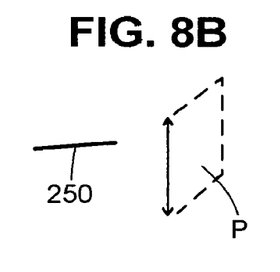
Figure 8C:
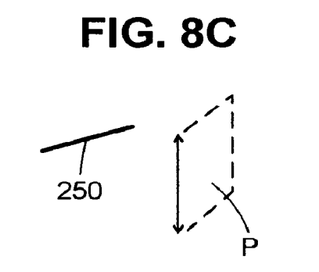

An easy method to establish the plumb line plane P intraoperatively, uses one or more suitable levels 230 to level an operating table 235. The table 235 includes one or more suitable tracking markers 240 to enable the system to track the position and orientation of the table 235. The table 235 is moved from a first height position A to a second height position B, and the table position is digitized at each of these positions A and B to establish the plumb line plane P. As discussed before a previously established functional frontal plane can now be tracked relative to the plumb line plane. The position and orientation of this plane may then be assessed relative to the plumb line plane P as illustrated in FIGS. 8A-8C.

For shoulders, the reference position is a neutral stance. This provides information relative to the appropriate positioning of the shoulder joint to maximize post operative flexibility and stability.

The surgical navigation system 100 includes appropriate software and circuitry to execute the disclosed functions. The computer program of the system may include any suitable user interface screens for executing the various features discussed herein.

INDUSTRIAL APPLICABILITY

Numerous modifications to the present invention will be apparent to those skilled in the art in view of the foregoing description. For example, virtual trials may be performed at any time during an arthroplasty procedure such as before of after dislocation of the limb from the joint. Accordingly, this description is to be construed as merely exemplary of the inventive concepts taught herein and is presented for the purpose of enabling those skilled in the art to make and use the invention and to teach the best mode of carrying out same. The exclusive rights to all modifications which come within the scope of the appended claims are reserved.

I claim:

1. A method of performing an arthroplasty of a stem-ball and socket joint with a surgical navigation system, the method comprising the steps of:
    digitizing landmarks to provide geometrical parameters of the joint and a limb depending therefrom, including digitizing aspects of a socket region and the stem of the limb;
    determining a range of motion parameter;
    placing a force sensor in the joint;
    collecting soft tissue tension force data from the force sensor while performing a range of motion analysis of the joint;
    determining a soft tissue tension parameter from the soft tissue tension force data;
    computing a functional goal based on landmark data, the range of motion parameter, the soft tissue tension parameter, and a database of potential implants;
    solving for a socket orientation to minimize impingement taking into account stability constraints based on an identified center of rotation of the socket;
    choosing an implant components combination and positioning to match the functional goal;
    solving for a socket position to minimize impingement taking into account stability constraints based on an identified stem position and the identified center of rotation of the socket;
    solving for a components combination and positioning to match the functional goal based on the socket position;

solving for a components combination and orientation to match the functional goal based on the socket position and the identified stem position;

choosing a final components combination and a final orientation of the components to match the functional goal;

preparing the joint to receive the final implant components; and installing the final implant components into the joint.

2. The method of claim 1, wherein a graph is displayed having axes showing positioning or sizing parameters of the components combination wherein a plurality of curves are displayed on the graph representing the effect of the geometrical parameters on anatomical, kinematical and tension values of the resulting joint configuration.

3. The method of claim 2, wherein the graph has first and second axes wherein the first axis is an amount of anteversion and a second axis is an amount of inclination of the socket and wherein a plurality of curves are displayed on the graph showing the effect of the anteversion and inclination on anatomical, kinematical, and tension values of the resulting joint configuration.

4. The method of claim 2, wherein the graph comprises first and second axes, wherein the first axis represents an amount of anteversion of the stem and the second axis represents an amount of neck angulation and socket offset, and wherein a plurality of curves is displayed on the graph showing the effect of the neck angulation and socket offset on anatomical, kinematical, and tension values of the resulting joint configuration.

5. The method of claim 2, wherein a marker displays the first socket components position relative to the plurality of curves.

6. The method of claim 1, wherein the joint is a hip joint.

7. The method of claim 1, wherein the joint is a shoulder joint.

8. A method of performing an arthroplasty of a ball and socket joint with a surgical navigation system, the method comprising the steps of:

digitizing geometrical parameters and range of motion data of the joint, wherein the step of digitizing is performed with the surgical navigation system;

measuring soft tissue tension force data from a force sensor in a trial implant in the joint during movement of the limb about the joint and calculating a soft tissue tension parameter from the soft tissue tension force data;

selecting a first socket position that provides a selected stability and potential for impingement and based at least in part on the soft tissue tension parameter;

establishing an acceptable tolerance range from the first socket position with regard to limb length, distal/proximal displacement, and lateral/medial displacement;

selecting an initial implant combination of components;

calculating and graphically displaying on a display mechanism attributes of the initial implant combination of components and a position of the initial implant combination of components relative to a range of additional potential attributes for additional potential implant combinations of components and for additional positions of the initial combination of components;

modifying the initial implant combination of components and the initial position of the initial combination of components to arrive at a final implant combination of components and a final position of the final combination of components for selected functional properties of the joint while staying within the tolerance range; and navigating the components to the final position with the aid of the surgical navigation system.

9. The method of claim 8, wherein the step of digitizing is performed using a surgical instrument, wherein the position of the surgical instrument is tracked by the surgical navigation system during the step of digitizing.

10. The method of claim 8, wherein a database of implant components is provided.

11. The method of claim 8, wherein a graph is displayed having axes showing geometrical parameters of the implant combination of components wherein a plurality of curves are displayed on the graph representing the effect of the geometrical parameters on anatomical, kinematical and tension values of the resulting joint configuration.

12. The method of claim 11, wherein the first axis is an amount of anteversion and a second axis is an amount of inclination of the socket and wherein a plurality of curves are displayed on the graph showing the effect of the anteversion and inclination of the socket on anatomical, kinematical and tension values of the resulting joint configuration.

13. The method of claim 11, wherein the first axis is an amount of anteversion of the stem and a second axis is an amount of neck angulation and socket offset and wherein a plurality of curves are displayed on the graph showing the effect of the anteversion of the stem and the amount of neck angulation and socket offset on anatomical, kinematical and tension values of the resulting joint configuration.

14. The method of claim 11, wherein a marker displays the first socket components position relative to the plurality of curves.

15. The method of claim 8, wherein the joint is a hip joint.

16. The method of claim 8, wherein the joint is a shoulder joint.

17. A method of performing an arthroplasty of a joint with a surgical navigation system, the method comprising the steps of:

establishing and tracking a functional plane of the joint relative to a predetermined at-rest position;

establishing and tracking a plumb line relative to the functional plane by leveling an operating table having one or more markers associated therewith for tracking the position of the operating table, linearly moving the leveled operating table between a first height position and a second height position, and tracking the position of at least one of the markers associated with the operating table at least at the first height position and the second height position;

preparing the joint to receive implant components;

choosing implant components that minimize impingement and maximize range of motion; and inserting the chosen implant components into the prepared joint.

18. The method of claim 17, wherein the functional plane is a frontal pelvic plane related to the stance of the pelvis while standing.

19. The method of claim 17, wherein the joint is a ball and socket joint.

20. The method of claim 17, wherein the joint is a hip joint.

21. The method of claim 17, wherein the method further includes the steps of inserting trial components into the prepared joint; and evaluating the trial components relative to predetermined goals.

* * * * *